April 17, 1962 R. W. CUMMING Plant Pat. 2,136
CHRYSANTHEMUM PLANT
Filed April 11, 1961
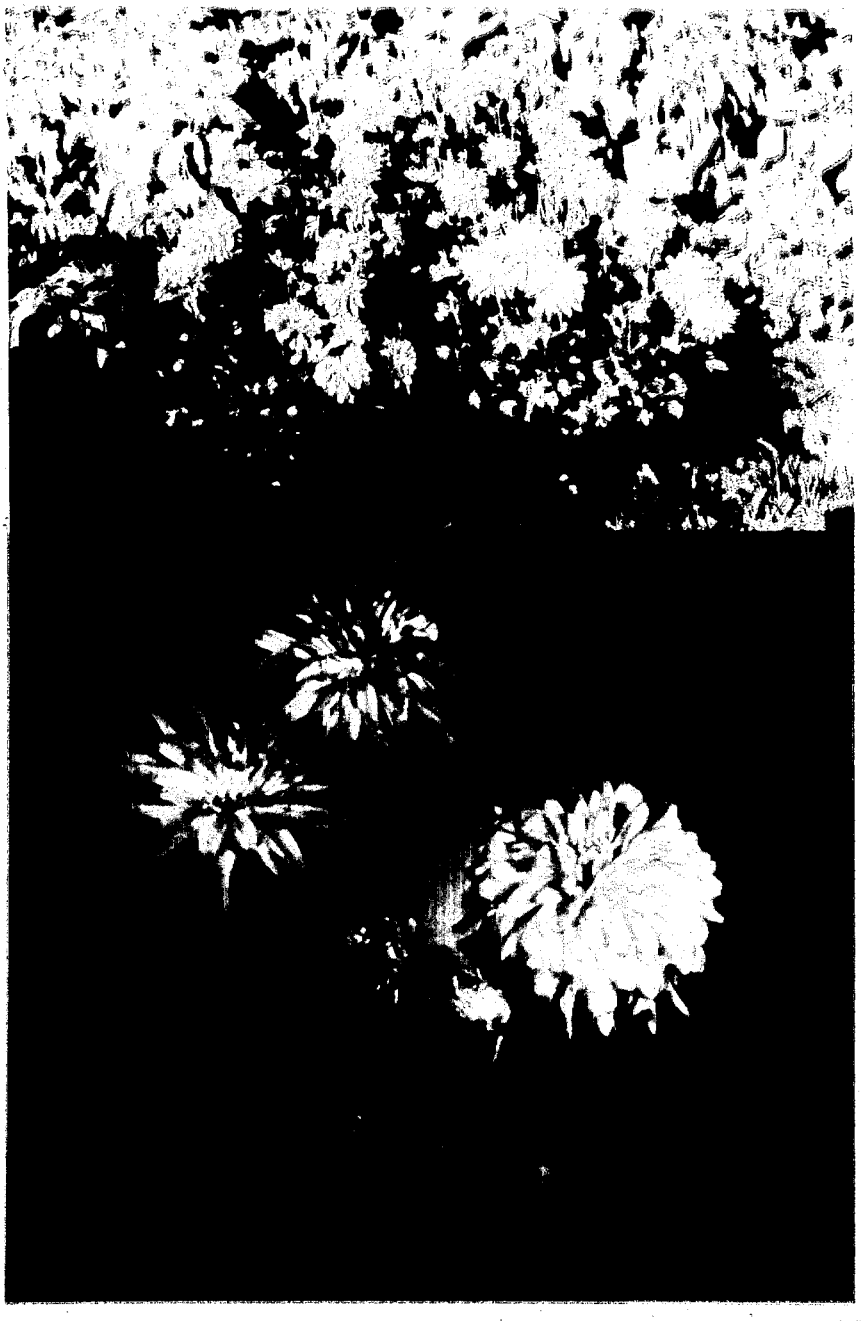
INVENTOR
Roderick W. Cumming
BY Robb & Robb
ATTORNEYS United States Patent Office Plant Pat. 2,136
Patented Apr. 17, 1962

2,136
CHRYSANTHEMUM PLANT

Roderick W. Cumming, Bristol, Conn., assignor to Bristol Nurseries, Inc., Bristol, Conn., a corporation of Connecticut Filed Apr. 11, 1961, Ser. No. 102,327
1 Claim. (Cl. 47—60)

The present invention relates to a new and distinct variety of chrysanthemum plant of the decorative class, which was originated by me by crossing two unnamed and unpatented chrystanthemum varieties. In this breeding, I used as one parent an unnamed chrysanthemum variety of the cushion type which bore Shrimp-Coral colored flowers. The other parent variety was of the decorative type that bore Rose-Pink colored flowers.

As the result of this breeding, I have succeeded in producing a new chrysanthemum variety which is endowed with the following unique combination of characteristics which are outstanding therein and which distinguish it from its parents, as well as from all other varieties of which I am aware:

(1) A stocky habit of plant growth;

(2) An early and prolific blooming habit;

(3) A distinctive, spectacular and vivid general color tonality of the flowers in which the colors are of varying blends of red tones, heightened by yellow and peach tints.

Asexual reproduction of the new variety by top cuttings, as performed by me at Bristol, Connecticut, shows that the aforementioned characteristics and distinctions come true to form and are established and transmitted through succeeding propagations.

The accompanying drawing shows typical specimens of the vegetative growth and flowers of my new chrysanthemum variety in various stages of developement, and as depicted in color as nearly true as it is reasonably possible to make the same in a color illustration of this character, with one of the views showing a clump or mound of the flowers and foliage, and the other view showing a few specimens of the flowers and foliage on a somewhat larger scale.

The following is a detailed description of my new chrysanthemum variety, with color terminology in accordance with the Horticultural Colour Chart, as promulgated by the British Colour Council of the Royal Horticultural Society, except where general color terms of ordinary dictionary significance are obvious, as based upon specimens grown at Bristol, Connecticut, and at numerous trial stations scattered over the United States:

Parentage: An unnamed Shrimp-Coral cushion type chrysanthemum variety × an unnamed Rose-Pink decorative type chrysanthemum variety.

Classification: Decorative.

Growth: Bushy; compact; attains a height of up to 2 feet.

Cold resistance: Average.

Blooming period: From about September 22 to killing frosts.

*Flower*

Bud:

*Color.*—When sepals first divide—Blood Red, Plate 820. When petals being to unfurl—Blood Red, Plate 820/2; frequently with center initially Empire Yellow, Plate 603. When half-blown: inside of petals—Orient Red, Plate 819; reverse of petals—Blood Red, Plate 820.

*Peduncle.*—Strength—strong; wiry. Color—Viridian Green, Plate 55/1.

Bloom:

*Size.*—Up to 3 inches in diameter.

*Stem.*—Strong; short; much-branched.

*Form.*—Decorative (informal).

*Petalage.*—Ample; broad; often irregularly strap-like.

*Color.*—Center of flower—Scarlet, Plate 19, flushed with Maize Yellow, Plate 607. Outer petals—Geranium Lake, Plate 20. Base of petals—Aureolin Yellow, Plate 3/2. Inside of petals—Poppy Red, Plate 16, flushed with Orange, Plate 12/2. Reverse of petals—from Geranium Lake, Plate 20, to Rose Madder, Plate 23, with the latter color predominating after cold weather. General tonality.—Bright Scarlet, flushed with peach and yellow.

*Petals.*—Texture—firm. Form—stubby at first, but later becoming elongated; rounded; informally strap-shaped.

*Fragrance.*—Initially above average.

*Plant*

Form: Bushy; broad; large; cushion type.

Growth: Compact; prolific.

Foliage:

*Size.*—Small; seldom over 2¼ inches long.

*Quantity.*—Above average.

*Color.*—Upper side—Emerald Green, Plate 758/1. Reverse side—Emerald Green, Plate 758.

*Texture.*—Firm; with waxen gloss.

I claim:

A new and distinct variety of chrysanthemum plant of the decorative class, substantially as herein shown and described, characterized particularly as to novelty by a stocky habit of plant growth, an early and prolific blooming habit, and a distinctive, spectacular and vivid general color tonality of the flowers in which the colors are of varying blends of red tones, heightened by yellow and peach tints.

No references cited.